United States Patent
Lehmann

(10) Patent No.: US 6,507,636 B1
(45) Date of Patent: Jan. 14, 2003

(54) RAPID X-RAY DIFFRACTION SCREENING METHOD OF POLYMORPH LIBRARIES CREATED IN MULTI-WELL PLATES

(75) Inventor: Christian W. Lehmann, Mülheim an der Ruhr (DE)

(73) Assignee: Studiengesellschaft Kohle mbH, Mulhiem an der Ruhr (DE)

( * ) Notice: Subject to any disclaimer, the term of this patent is extended or adjusted under 35 U.S.C. 154(b) by 0 days.

(21) Appl. No.: 09/501,634

(22) Filed: Feb. 10, 2000

(51) Int. Cl.⁷ .............................................. G01N 23/20
(52) U.S. Cl. ............................ 378/79; 378/73; 378/208
(58) Field of Search ............................ 378/73, 79, 208

(56) References Cited

U.S. PATENT DOCUMENTS

| | | | | |
|---|---|---|---|---|
| 4,278,883 A | * | 7/1981 | Hathaway et al. | 250/277 |
| 4,634,599 A | * | 1/1987 | Uzgiris | 427/2 |
| 4,862,488 A | * | 8/1989 | Schiller | 378/81 |
| 4,961,210 A | * | 10/1990 | Fatemi | 378/73 |
| 5,221,410 A | * | 6/1993 | Kushner et al. | 156/600 |
| 5,414,747 A | * | 5/1995 | Ruud et al. | 378/73 |
| 5,597,457 A | * | 1/1997 | Craig et al. | 204/165 |
| 6,005,914 A | * | 12/1999 | Quinn et al. | 378/81 |
| 6,111,930 A | * | 8/2000 | Schipper | 378/79 |
| 6,168,914 B1 | * | 1/2001 | Campbell et al. | 435/4 |

* cited by examiner

Primary Examiner—Robert H. Kim
Assistant Examiner—Jurie Yun
(74) Attorney, Agent, or Firm—Norris McLaughlin & Marcus

(57) ABSTRACT

Method and device for rapid characterization of arrays of crystalline, polycrystalline or amorphous materials; in particular for the formation and X-ray diffraction analysis of polymorph libraries and the discovery of new crystal forms. According to one aspect, a multi-well plate comprising a masking plate with an array of openings and a removable base plate is used to crystallize precipitates. X-ray diffraction analysis is performed by scanning an X-ray beam over the base plate and recording diffractograms of the crystalline precipitates.

19 Claims, 1 Drawing Sheet

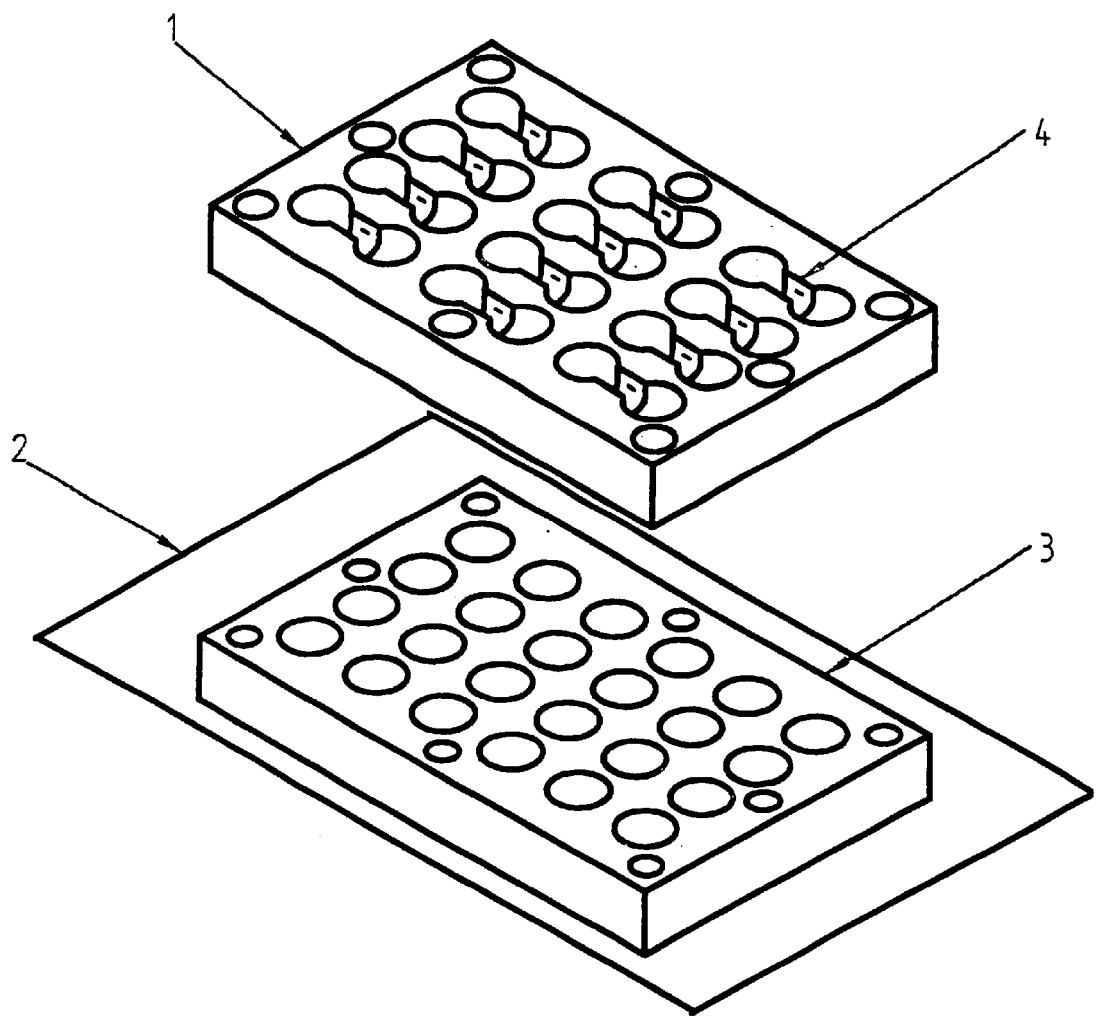

RAPID X-RAY DIFFRACTION SCREENING METHOD OF POLYMORPH LIBRARIES CREATED IN MULTI-WELL PLATES

FIELD OF THE INVENTION

The present invention generally relates to the characterization of crystalline materials that have been formed on a single substrate surface at predefined positions. More specifically, the invention is directed to the rapid screening of polymorph libraries using X-ray micro-diffraction methods.

BACKGROUND OF THE INVENTION

Polymorphism is the commonly used description for the occurrence of multiple crystal forms of the same chemical compound, distinguishable through physical characterization methods like melting point, rate of dissolution, infra-red and raman spectroscopy, and most pronounced single crystal and powder X-ray diffraction. (W. C. McCrone in "Physics and Chemistry of the Organic Solid State Vol. 2" Eds. D. Fox, M. M. Labes, A. Weissberger, Interscience New York, (1965) 725–767).

Since different crystal forms within one polymorphic system exhibit different physical properties i.e. rate of dissolution (which in turn affects bio-availability), melting point, hygroscopic behavior or pressure stability, identifying different crystal forms is increasingly important in the pharmaceutical industry during the drug product process development stage but also during the drug substance research stage.

Polymorph screens are conducted through crystallization experiments by systematic variation of parameters like solvent, temperature or crystallization method, and crystalline products are characterized using thermo-microscopy, spectroscopic and diffraction methods. The combination of different solvents, crystallization methods and temperatures results in several dozen to several hundred possibly even several thousands of crystallization attempts.

Multi-well plates are the preferred containment for these crystallization experiments, combining the advantage of easy storage and transportability with the option to work with small quantities of substance on the micro-gram scale. With conventional multi-well plates the problem remains however that for crystalline, polycrystalline or amorphous materials, samples have to be removed from the wells and transferred to special sample holders. This procedure is unsuitable for high throughput screening since larger amounts of sample are necessary and only a few samples can be analysed per day and diffractometer.

In the field of combinatorial inorganic and materials chemistry a similar challenge exists for the rapid characterization of crystalline reaction products. Recently, a microreactor design was reported for generating combinatorial material libraries through chemical reactions and subsequently analysing these using X-ray diffraction (J. Klein, C. W. Lehmann, H.-W. Schmidt, W. F. Maier, Angew. Chem. Int. Ed. 37, (1998), 3369–3372, and PCT Publication No. EP99/03287).

When using conventional, commercially available multi-well plates for crystallization experiments, then a subsequent diffraction experiment, where the crystalline, polycrystalline or amorphous materials remain in the multi-well plate, faces the following problems. In the case of multi-well plates with permanently affixed side walls the angular range accesssible to the incident and diffracted X-ray beam is determined by the ratio of well diameter to well depths. In most multi-well plates in the prior art this ratio is optimised to place a maximum number of wells onto a given surface area while maintaining a specific volume in each well. Assuming typically diameter to depth ratios between 4:1 and 1:4, it follows that wells with circular cross-section cover at most the angular range of 53 to 180° Bragg-angle 2È and 176 to 180° Bragg-angle 2È respectively, for a reflection geometry diffraction experiment, based on an infinitely small X-ray beam and sample size.

Similar considerations hold for X-ray diffraction experiments in transmission geometry. Here the fixed side wall limits the possible ù-rotation of the sample, while particular requirements must be placed on the properties of the bottom face of the multi-well plates in order to avoid scattering artifacts from the sample support.

SUMMARY OF THE INVENTION

The present invention provides a device in form of a multi-well plate with detachable base plate, for producing an array of crystalline, polycrystalline or amorphous samples. The present invention also provides a method for characterizing such an array that has been formed on a substrate at predefined positions using X-ray micro-diffraction.

More specifically, the invention is directed to the rapid screening of polymorph libraries, prepared using standard crystallization techniques, including but not limited to solvent evaporation, gas phase vapor diffusion, temporal and spatial temperature gradients.

In one embodiment, the multi-well plate is constructed in such a way, that crystalline or polycrystalline precipitates form on the removable substrate, which acts simultaneously as the bottom face to each well, which allows depending on the choice of substrate the characterization of said precipitates by X-ray diffraction in either transmission or reflection geometry.

In a specific configuration the base plate is made of single crystal silicon oriented in the (1 1 1) direction in order to minimise diffuse X-ray scattering originating from the sample support. In this configuration X-ray diffraction analysis is carried out in reflection geometry.

In yet another specific configuration the base plate is made from optically transparent sapphire, shown to be virtually free of X-ray scattering artifacts in the background of the diffractogram. In this configuration X-ray diffraction analysis is also carried out in reflection geometry.

In a further specific configuration the base plate is made from an optically and X-ray transparent polymer film including but not limited to polyacetate for visual inspection of crystalline samples using optical microscopy. X-ray diffraction characterization of the formed crystalline or polycrystalline materials can be carried out either in transmission or in reflection geometry.

X-ray diffractograms from each sample spot deposited are obtained by placing the single substrate into a parallel X-ray beam, by means of a xyz-sample translation stage. Diffracted X-rays are detected by an area detector, for example using a multi-wire gas proportional detector. Diffraction images are converted to diffractograms tabulating intensity versus Bragg angle 2è. The identity of or difference between characterized crystalline forms is established through standard pattern matching procedures.

BRIEF DESCRIPTION OF THE DRAWING

FIG. 1 is a perspective view of one configuration of a multi-well plate according to the present invention. The masking plate 1 is secured to the base plate 2, which is made from a thin polymer film, via a separate pressurizing plate 3. Channels 4 interconnect neighboring wells.

DETAILED DESCRIPTION OF THE INVENTION AND PREFERRED EMBODIMENTS

Multi-well Plate Description

The multi-well plate used in the present invention comprises the following main components: a removable base plate connected to a masking plate with openings forming an array. The base plate and masking plate are connected in such way that a liquid-tight connection is formed. The masking plate is covered by a removable lid providing a gas tight seal between the individual voids created by the composite of base plate, masking plate and lid and between said voids and the surrounding atmosphere. The material the base plate is made of, can be selected from a variety of materials depending on the geometry used in the X-ray diffraction experiment. These materials must exhibit chemical and mechanical stability towards the chemical substances used in the crystallization experiment. The material the masking plate is made of, can be selected from a variety of materials exhibiting chemical and mechanical stability towards the chemical substances used in the crystallization experiment. The material the lid is made of, can be selected from materials which are not penetrated by air and vapors of the solvents used in the crystallization experiment. Generally an optically transparent material is preferred for the base plate as well as the lid, as it allows the observation of individual wells using light transmission microscopy.

In one embodiment suited for subsequent X-ray diffraction analysis in reflection geometry, the base plate is made from a disc cut from a single crystal including but not limited to silicon or quartz. An alternative material for the base plate is sapphire. This plate is secured to the masking plate via a seperate additional pressurising plate which distributes an equal pressure over the whole contact area of all three plates. The connection is made by means of several bolts all tightened to the same tension. Depending on the surface finish of the top surface of the base plate and the bottom surface of the masking plate, an additional gasket is inserted, repeating the pattern of the masking plate, or individual gaskets are inserted at the position of each opening of the masking plate. The lid is made preferably from an optically transparent material to enable visual observation of the wells. Again depending on the surface finish of the top surface of the masking plate and the bottom surface of the lid plate an additional gasket is inserted, repeating the pattern of the masking plate, or individual gaskets are inserted at the position of each opening of the masking plate.

In another preferred embodiment, suited for subsequent X-ray diffraction analysis in transmission geometry the base plate is made from a thin polymer film consisting of polyacetate, which exhibits in thicknesses as low as 0.015 mm no amorphous background scattering or regions in the diffractogram associated with crystallinity of the polymer. Other polymer films are also suitable for the purpose of forming the base plate, also some characteristic X-ray scattering will normally be observed. The polymer film is secured to the masking plate via a separate additional pressurising plate which distributes an equal pressure over the whole contact area of the polymer film and the masking plate. Gaskets as described above are used where necessary. In order to reduce X-ray absorption by the base plate a material with as low as possible an average atomic number and as low as mechanically and chemically possible thickness is used.

In a specific configuration of the masking plate, which can be combined with either type of base plate, the masking plate is made from a metallic material in order to conduct heat efficiently. In this specific form of the masking plate, optional heat exchangers are connected to the masking plate, in order to control and to change the temperature of the multiwell plate during the crystallization experiment. A temperature gradient is formed in a transverse direction along the masking plate by applying two different temperatures to either end of the masking plate.

In a further specific configuration of the metallic masking plate, the openings are lined with polytetrafluoroethylene (PTFE), or another chemically inert polymer to enhance the chemical resistivity of the masking plate while preserving the heat conducting properties.

Library Characterization

Arrays of crystalline, polycrystalline or even amorphous precipitates are transferred to the X-ray microdiffractometer for the purpose of characterization using X-ray diffraction.

For this purpose the base plate is separated from the remaining components of the multi-well plate. The essentially flat geometry of the base plate then permits the incident and diffracted X-ray beams to access the sample over a wide angular range in the case of reflection geometry. In the case of thin polymer film base plates used for transmission geometry, these are positioned perpendicular to the X-ray beam via a clamping frame attached to the translation stage of the diffractometer.

Following further from these considerations specific requirements are placed upon the X-ray microdiffractometer. These requirements are the detection of micro-gram quantities of crystalline, polycrystalline or amorphous sample, automated movement of the sample support to the location of each predefined multi-well position, and large angular range of Bragg-angles including at least 4 to 120° $2\Theta$ combined with narrow X-ray beam diameter in the case of reflection geometry.

The small beam diameter is needed to match the area illuminated by the X-ray beam to the dimensions of the sample when working in reflection geometry at small incident beam angles. The xyz-stage allows to analyse sequentially and fully automated each crystallization well.

Since no sample preparation, i.e. grinding is applied, the sample will necessarily show spotty diffraction rings, possibly suffer from preferred orientation and in some cases show pronounced single crystal reflection. However the area detector covers a considerable segment of the Laue-cones, which allows for averaging out the above effects during the integration process, which in turn results in a conventional diffractogram.

The recorded diffractograms can be compared to collections of known or of calculated diffractograms in order to confirm the identity of the obtained crystal form. The comparisons can be made visually or by computer algorithms.

EXAMPLE

The following example illustrates the preparation of an array of polycrystalline material from a single substance using a multi-well plate, for the subsequent characterization of said material by X-ray diffraction analysis.

The compound 4'-methylchalcone 1 is prepared according to the description of Kostanecki, St. v. and Rossbach G. (Chemische Berichte 29, 2245–2247, 1896). Recrystallization from ethanol yields 1 in 94.5% purity by GC.

The multi-well plate used in this example consists of a 0.03 mm thick polyacetate film sandwiched between two 10 mm thick brass plates, held in place by six M6 bolts. Both brass plates feature a 5×8 array of matching holes with 6 mm diameter. The upper brass plate, the masking plate, also features on the top face channels with semicircular cross-section connecting adjoining holes in pairs. The bottom face of the masking plate is equipped with O-rings providing individual seals between the masking plate and the polymer film.

100 µl saturated ethanolic solution of 1 are pipetted into the wells of the multi-well plate and covered with perforated parafilm®. The solvent evaporates completely within 24 h and polycrystalline precipitates form on the bottom face of the filled wells.

The polymer film with the attached crystalline precipitates is removed from the multi-well plate assembly and positioned into the X-ray beam of a Bruker AXS GADDS (Bruker AXS Inc., 5465 East Cheryl Parkway, Madison, Wis. 53711, United States of America) diffractometer by means of a clamping frame.

In the specific configuration the diffractometer consists of a sealed Copper-radiation X-ray tube, crossed multi-layer parallel beam X-ray optics (Göbel mirrors) with a variable X-ray beam diamter between 0.05 mm and 0.5 mm, xyz-motorized programmable sample translation stage and photon counting multi-wire gas proportional X-ray detector. The recording of diffraction patterns at angles as low as 3 deg. 2-theta (for Cu-radiation) requires also a shortened X-ray collimator. The spatial resolution of the area detector is about 0.1 mm in the 1024×1024 pixel storage mode and diffraction patterns are recorded typically at 200 mm distance; this distance can be varied between 60 and 300 mm. Part of the system is also an alignment laser and video microscope which permits to center the desired part of the sample exactly in the center of the goniometer.

A diffraction pattern using Cu-Ká radiation (ë=1.5483 Å) representative of the whole area of one well is recorded using the translation mechanism of the diffractometer. This procedure is repeated for all other well areas according to the predefined well pattern.

Further Examples of Library Preparation

Arrays of crystalline or polycrystalline precipitates are created by depositing a solution containing the dissolved substance to be crystallized in one well of the multi-well plate. Further wells are filled with the same substance dissolved either in the same solvent at a different concentration or in a different solvent or mixture of at least two different solvents. By changing at least one crystallization parameter either continously with time and or space, or changing at least one crystallization parameter suddenly, crystallization is initiated and allowed to progress. Crystallization parameters include but are not limited to, change of solubility of the substance by change of concentration of the substance in solvent through solvent evaporation; change of solubility of the substance by adding precipitant; change of solubility of the substance through change of temperature.

In one embodiment the rate of evaporation is controlled by differently sized appertures fixed to the top site of the multi-well plate.

In another embodiment precipitants are added in one of several ways depending on the difference in density and desired rate of mixing between the two solvent systems. Either by layering one solvent upon the other, or by allowing solvent vapor to diffuse between wells connected pairwise, above the meniscus of the solvents, and sealing of these well-pairs to the surrounding atmosphere to prevent loss of solvent.

In an alternative embodiment the temperature of multi-well plate is changed either with a time dependent gradient or sudden change or with a spatial gradient which puts different wells of the multi-well plate at different temperatures.

What is claimed is:

1. A method for characterizing crystalline, polycrystalline or amorphous materials in an array of said materials comprising:
   a) providing a multi-well plate comprising:
      i) a base plate; and
      ii) a masking plate with an array of openings;
      wherein said base plate is separable from said masking plate;
   b) forming said materials through crystallization or precipitation, on said multi-well plate so that each material is located in a predefined area of said base plate;
   c) separating said base plate from said masking plate; and
   d) characterizing said materials using X-ray diffraction, analyzing each predefined location of said array in subsequent steps directly on the base plate.

2. The method of claim 1, wherein said material consists of a single chemical compound, and wherein the conditions of crystallization or precipitation are varied depending on the position of the predefined area on the base plate.

3. The method of claim 2, wherein the single chemical compound is an organic compound or natural product.

4. The method of claim 2, wherein the single chemical compound is a pharmaceutical drug substance.

5. The method of claim 1, wherein the said material found on the base plate is placed in reflection geometry into the X-ray beam of an X-ray diffractometer and is moved by means of a translation mechanism into the X-ray beam.

6. The method of claim 1, wherein the said material found on the base plate is placed in transmission geometry into the X-ray beam of an X-ray difractometer and is moved by means of a translation mechanism into the X-ray beam.

7. A multi-well plate for the formation and X-ray diffractometric analysis of an array of crystalline, polycrystalline or amorphous materials comprising:
   a) a base plate; and
   b) a masking plate with an array of openings;
   said base plate being separable from aid masking plate.

8. The multi-well plate of claim 7, wherein the masking plate is made from metal.

9. The multi-well plate of claim 7, further comprising channels connecting adjoining openings pairwise in such way to enable an exchange of gas but not liquid between said openings.

10. The multi-well plate of claim 7, wherein the openings are coated with a chemically inert polymer, or wherein said openings are lined with chemically inert polymer sleeves.

11. The multi-well plate of claim 10, wherein said chemically inert polymer is polytetrafluoroethylene.

12. The multi-well plate of claim 7, wherein the base plate is made from a single crystal plate.

13. The multi-well plate of claim 12, wherein the single crystal plate is made from silicon or quartz.

14. The multi-well plate of claim 7, wherein the base plate is made from an optically transparent plate of sapphire.

15. The multi-well plate of claim 7, wherein the base plate is made from a polymer film which is transparent for X-rays with a wavelength in the range between 0.45 and 2.5 Å, and which is chemically resistant to organic solvents and water.

16. The multi-well plate of claim 15, wherein the polymer film is made from polyacetate with a thickness between 0.1 $\mu$m and 100 $\mu$m.

17. The multi-well plate of claim 7, further comprising a pressurising plate with an array of openings matching the pattern of the openings of the masking plate, wherein said pressurising plate is connected removably to the multi-well plate assembly.

18. The multi-well plate of claim 7, further comprising one or more connectors for fitting heat-exchangers to the masking plate.

19. The multi-well plate of 18, wherein said heat-exchangers comprise metal rods through which a liquid flows.

* * * * *

UNITED STATES PATENT AND TRADEMARK OFFICE
CERTIFICATE OF CORRECTION

PATENT NO. : 6,507,636 B1
DATED : January 14, 2003
INVENTOR(S) : Lehmann

It is certified that error appears in the above-identified patent and that said Letters Patent is hereby corrected as shown below:

<u>Column 6,</u>
Line 43, "difractometer" should read -- diffractometer --.
Line 49, "b) a masking plate with an array of openings;" should read -- b) a masking plate with an array of openings permitting the introduction of one or more crystalline, polycrystalline or amorphous materials to the base plate when the masking plate is connected to the base plate; and c) one or more crystalline, polycrystalline or amorphous materials applied to the base plate; --.
Line 50, "from aid" should read -- from said --.

Signed and Sealed this

Second Day of May, 2006

JON W. DUDAS
*Director of the United States Patent and Trademark Office*